(12) United States Patent
Wan et al.

(10) Patent No.: US 11,629,359 B2
(45) Date of Patent: Apr. 18, 2023

(54) PLASMA MEMBRANE INTRINSIC AQUAPORIN FOR ABSORBING AND TRANSPORTING NEONICOTINOID INSECTICIDES, AND CODING GENE AND USE THEREFOR

(71) Applicant: JIANGSU ACADEMY OF ARGRICULTURAL SCIENCES, Nanjing (CN)

(72) Inventors: Qun Wan, Nanjing (CN); Xiangyang Yu, Nanjing (CN); Yixin Li, Nanjing (CN); Jinjin Cheng, Nanjing (CN); Ruohan Wu, Nanjing (CN)

(73) Assignee: JIANGSU ACADEMY OF AGRICUULTURAL SCIENCES, Nanjing (CN)

( * ) Notice: Subject to any disclaimer, the term of this patent is extended or adjusted under 35 U.S.C. 154(b) by 0 days.

(21) Appl. No.: 17/426,942

(22) PCT Filed: Aug. 26, 2020

(86) PCT No.: PCT/CN2020/111211
§ 371 (c)(1),
(2) Date: Jul. 29, 2021

(87) PCT Pub. No.: WO2021/139170
PCT Pub. Date: Jul. 15, 2021

(65) Prior Publication Data
US 2022/0056471 A1 Feb. 24, 2022

(30) Foreign Application Priority Data
Jul. 27, 2020 (CN) .......................... 202010734390.0

(51) Int. Cl.
*C12N 15/82* (2006.01)
*A01N 63/50* (2020.01)
*C07K 14/415* (2006.01)

(52) U.S. Cl.
CPC ......... *C12N 15/8286* (2013.01); *A01N 63/50* (2020.01); *C07K 14/415* (2013.01)

(58) Field of Classification Search
None
See application file for complete search history.

(56) References Cited

U.S. PATENT DOCUMENTS 8,110,724 B2 * 2/2012 Wang .................. C07K 14/415
800/290

FOREIGN PATENT DOCUMENTS

| CN | 1884542 | 12/2006 |
| CN | 101671677 | 3/2010 |
| CN | 101787074 | 7/2010 |
| CN | 101939435 | 2/2011 |
| CN | 102382185 | 3/2012 |

OTHER PUBLICATIONS

Kaldenhoff et al, 2006, Acta Physiol. 187:169-176.*
Gao et al (1999, Plant Mol. Biol. 40:635-644).*
Yu et al (2005, Plant Sci. 169:647-656).*
Johanson U. The complete set of genes encoding major intrinsic proteins in *Arabidopsis* provides a framework for a new nomenclature for major intrinsic proteins in plants. Plant Physiology, 2001, 126(4):1358-69.
Bienert G P, Bienert M D, Jahn T P, et al. Solanaceae XIPs are plasma membrane aquaporins that facilitate the transport of many uncharged substrates. Plant Journal, 2011, 66(2):306-317.
Li T, Choi W G, Wallace I S, et al. *Arabidopsis thaliana* NIP7;1: an anther-specific boric acid transporter of the aquaporin superfamily regulated by an unusual tyrosine in helix 2 of the transport pore. Biochemistry, 2011, 50(31):6633-6641.
Terashima I, Ono K. Effects of HgCl2 on CO2 dependence of leaf photosynthesis: evidence indicating involvement of aquaporins in CO2 diffusion across the plasma membrane. Plant Cell Physiology, 2002, 43(1): 70-78.
Heinen R B, Bienert G P, Cohen D, et al. Expression and characterization of plasma membrane aquaporins in stomatal complexes of *Zea mays* Plant Molecular Biology, 2014, 86(3):335-350.
Chen Y, Sun S K, Tang Z, et al. The Nodulin 26-like intrinsic membrane protein OsNIP3;2 is involved in arsenite uptake by lateral roots in rice. Journal of Experimental Botany, 2017, 68(11):3007-3016.
Sun S K, Chen Y, Che J, et al. Decreasing arsenic accumulation in rice by overexpressing OsNIP1;1 and OsNIP3;1 through disrupting arsenite radial transport in roots. New Phytologist, 2018.
Moller I M. Plant mitochondria and oxidative stress: electron transport, NADPH turnover, and metabolism of reactive oxygen species. Annual Review of Plant Biology, 2001, 52(4):561-591.
Liu T, et al. Unconventionally secreted effectors of two filamentous pathogens target plant salicylate biosynthesis. Nat Commun 5, 4686. 2014.
He Lin, Jiang Lili, Wang Yucheng, Analysis of the stress tolerance of Tamarix thioredoxin peroxidase (ThPrx1) gene transformed into yeast, Journal of Northeast Forestry University, 2011, vol. 39. No. 4, 101-104.

(Continued)

*Primary Examiner* — Anne Kubelik
(74) *Attorney, Agent, or Firm* — Treasure IP Group, LLC

(57) ABSTRACT

The disclosure discloses a Chinese cabbage plasma membrane intrinsic aquaporin, having an amino acid sequence as set forth in SEQ ID NO. 2, and the nucleotide sequence of the encoding gene BraPIP2;1 thereof is as set forth in SEQ ID NO. 1. The plasma membrane intrinsic aquaporin has the characteristic of sensitively responding to neonicotinoid insecticides (thiamethoxam, imidacloprid, etc.) in the external environment. At the same time, it has the function of mediating transmembrane transport of the neonicotinoid insecticides, promoting accumulation of the neonicotinoid insecticides in plant roots and leaves, which has important application value in guiding efficient and simple use of pesticides, development of new systemic pesticides, etc.

Figure 1:
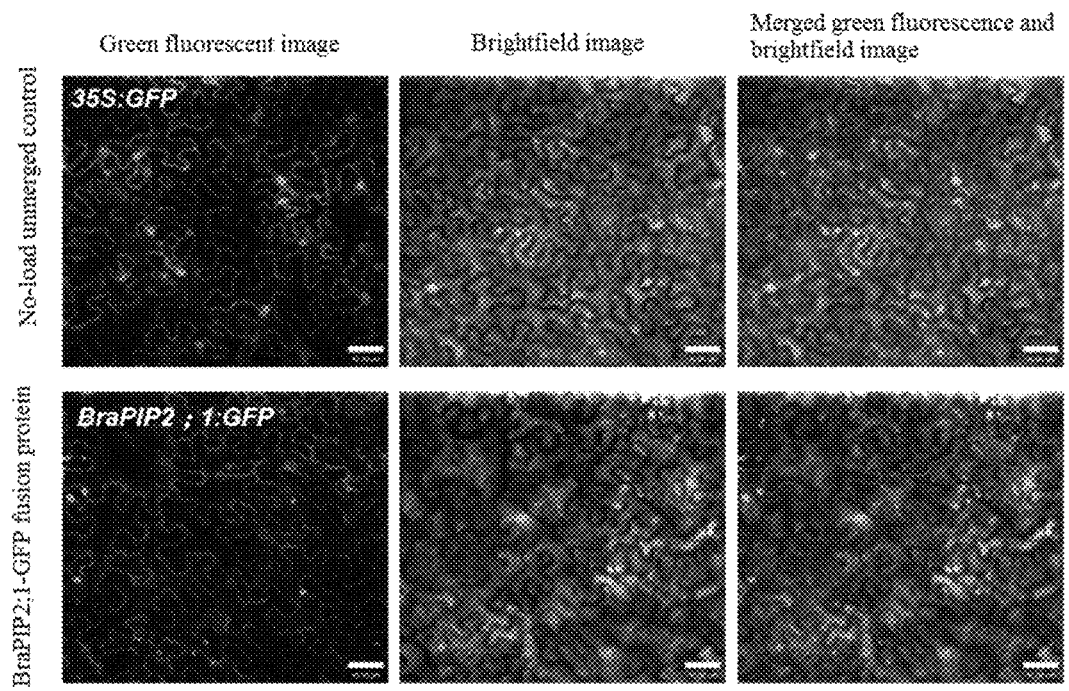

4 Claims, 5 Drawing Sheets
Specification includes a Sequence Listing.

(56) References Cited

OTHER PUBLICATIONS

Valvekens, D., van Montagu, M., and Lijsebettens, M. V. (1988). Agrobacterium tumefaciens-mediated transformation of *Arabidopsis thaliana* root explants by using kanamycin selection. Proc. Natl. Acad. Sci. USA 85, 5536-5540.

"*Brassica napus* aquaporin PIP2-I (LOC 106382572), mRNA, Accession No. NM_001316255.1." NCBI_GENBANK., May 5, 2019 (May 5, 2019).

Maurel. C. et al. "Aquaporins in Plants." Physiol. Rev., vol. 95, Sep. 2, 2015 (Sep. 2, 2015).

\* cited by examiner

SEQUENCE LISTING

```
<160> NUMBER OF SEQ ID NOS: 8

<210> SEQ ID NO 1
<211> LENGTH: 864
<212> TYPE: DNA
<213> ORGANISM: Artificial Sequence
<220> FEATURE:
<223> OTHER INFORMATION: synthetic gene

<400> SEQUENCE: 1
atggcgaagg acgtggaagc cgtttccgga gaagggtttc agacaagaga ctatcaagat     60
ccaccgccag cgcctctgtt tgacccggcg gagctgacca agtggtcttt ctacagagca    120
gtcatcgctg agttcgtagc tactctcctc ttcctgtaca tcaccgtttt gacagtcatc    180
ggttacaaga ttcagaccga tagtactgcc ggcggcgttg actgcggtgg agttggtatc    240
ctaggtatcg cttgggcttt tggtggcatg atcttcatcc ttgtctactg caccgccggt    300
atctctggtg gtcacattaa cccggcagtg acatttgggc tactcttagc gcgtaaagtg    360
tccttggtaa gagccatttt gtacatggta gctcagtgtt tgggtgcgat atgcggagtt    420
gggttcgtca aagccttcca aagctcttac tacgtccgtt acggtggtgg agcaaactct    480
ctagccgacg gctacagcac aggaaccgga ctagccgcag agatcattgg tactttcgtt    540
cttgtctaca ccgtcttctc cgccactgac cctaaacgta gtgccagaga ctcccacgtc    600
ccagtgttgg cgccacttcc cattggattt gcggtgttca tggtgcactt ggctaccatt    660
cccatcactg gaactggaat caacccggca aggagtttcg gagcagccgt tatcttcaac    720
gagagcaagc catgggatga ccactggata ttttgggtgg gaccattcgt tggagctgcg    780
atagctgcat tctaccacca gttcgttttg agggcttcag gttccaagtc tctcggatct    840
ttcagaagtg ctgccaacgt ttaa                                           864

<210> SEQ ID NO 2
<211> LENGTH: 287
<212> TYPE: PRT
<213> ORGANISM: Artificial Sequence
<220> FEATURE:
<223> OTHER INFORMATION: From cabbage

<400> SEQUENCE: 2

Met Ala Lys Asp Val Glu Ala Val Ser Gly Glu Gly Phe Gln Thr Arg
1               5                   10                  15

Asp Tyr Gln Asp Pro Pro Pro Ala Pro Leu Phe Asp Pro Ala Glu Leu
            20                  25                  30

Thr Lys Trp Ser Phe Tyr Arg Ala Val Ile Ala Glu Phe Val Ala Thr
        35                  40                  45

Leu Leu Phe Leu Tyr Ile Thr Val Leu Thr Val Ile Gly Tyr Lys Ile
    50                  55                  60

Gln Thr Asp Ser Thr Ala Gly Gly Val Asp Cys Gly Gly Val Gly Ile
65                  70                  75                  80

Leu Gly Ile Ala Trp Ala Phe Gly Gly Met Ile Phe Ile Leu Val Tyr
                85                  90                  95
```

```
Cys Thr Ala Gly Ile Ser Gly Gly His Ile Asn Pro Ala Val Thr Phe
                100                 105                 110
Gly Leu Leu Leu Ala Arg Lys Val Ser Leu Val Arg Ala Ile Leu Tyr
            115                 120                 125
Met Val Ala Gln Cys Leu Gly Ala Ile Cys Gly Val Gly Phe Val Lys
130                 135                 140
Ala Phe Gln Ser Ser Tyr Tyr Val Arg Tyr Gly Gly Ala Asn Ser
145                 150                 155                 160
Leu Ala Asp Gly Tyr Ser Thr Gly Thr Gly Leu Ala Ala Glu Ile Ile
                165                 170                 175
Gly Thr Phe Val Leu Val Tyr Thr Val Phe Ser Ala Thr Asp Pro Lys
            180                 185                 190
Arg Ser Ala Arg Asp Ser His Val Pro Val Leu Ala Pro Leu Pro Ile
        195                 200                 205
Gly Phe Ala Val Phe Met Val His Leu Ala Thr Ile Pro Ile Thr Gly
    210                 215                 220
Thr Gly Ile Asn Pro Ala Arg Ser Phe Gly Ala Ala Val Ile Phe Asn
225                 230                 235                 240
Glu Ser Lys Pro Trp Asp Asp His Trp Ile Phe Trp Val Gly Pro Phe
                245                 250                 255
Val Gly Ala Ala Ile Ala Ala Phe Tyr His Gln Phe Val Leu Arg Ala
            260                 265                 270
Ser Gly Ser Lys Ser Leu Gly Ser Phe Arg Ser Ala Ala Asn Val
        275                 280                 285

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
atggcgaagg acgtggaagc                                              20

<210> SEQ ID NO 4
<211> LENGTH: 22
<212> TYPE: DNA
<213> ORGANISM: Artificial Sequence
<220> FEATURE:
<223> OTHER INFORMATION: primer

<400> SEQUENCE: 4
ttaaacgttg gcagcacttc tg                                           22

<210> SEQ ID NO 5
<211> LENGTH: 22
<212> TYPE: DNA
<213> ORGANISM: Artificial Sequence
<220> FEATURE:
<223> OTHER INFORMATION: primer

<400> SEQUENCE: 5
tcactggaac tggaatcaac cc                                           22

<210> SEQ ID NO 6
<211> LENGTH: 21
<212> TYPE: DNA
<213> ORGANISM: Artificial Sequence
<220> FEATURE:
```

-continued

```
<223> OTHER INFORMATION: primer

<400> SEQUENCE: 6
cctgaagccc tcaaaacgaa c                                             21

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
actgggtgtt ttgggttggg                                               20

<210> SEQ ID NO 8
<211> LENGTH: 22
<212> TYPE: DNA
<213> ORGANISM: Artificial Sequence
<220> FEATURE:
<223> OTHER INFORMATION: primer

<400> SEQUENCE: 8
tgaaggggat tgctctgatg ac                                            22
```

PLASMA MEMBRANE INTRINSIC AQUAPORIN FOR ABSORBING AND TRANSPORTING NEONICOTINOID INSECTICIDES, AND CODING GENE AND USE THEREFOR

CROSS REFERENCE TO RELATED APPLICATION

This application is a national stage application of PCT/CN2020/111211, which claims priority to Chinese Application No. 202010734390.0, filed on Jul. 27, 2020. The Chinese Application and international application are incorporated herein by reference in their entireties.

A sequence listing in the ASCII text file with a " " extension via EFS-Web is herein incorporated by reference. Said sequence listing in the ASCII text file with a ".txt" extension is named "21218YWX_Untitled_ST25", date of creation is Sep. 10, 2021, size is 5 KB.

TECHNICAL FIELD

The disclosure belongs to the technical field of biology, and in particular relates to a plasma membrane intrinsic aquaporin derived from Chinese cabbage and application thereof in improving the transport and utilization efficiency of crop neonicotinoid insecticides.

BACKGROUND ART

Neonicotinoid insecticides (such as thiamethoxam, imidacloprid, acetamiprid, nitenpyram and dinotefuran) are synthetic compounds similar to the natural insecticide nicotine in structure, and target nicotinic acetylcholine receptors (nAChRs) in the central nervous system of insects. Therefore, the neonicotinoid insecticides are more selective and less toxic to non-target organisms than traditional insecticides. The neonicotinoid insecticides have high polarity, high solubility, and strong systemic action, and are used for stem and leaf spray, soil irrigation and seed treatment. After application, the neonicotinoid insecticides are transported by leaves or roots quickly to all parts of the plant through systemic action, and can effectively control aphids, leaf miners and other pests. The neonicotinoid insecticides have been widely used worldwide, and account for 24% of the insecticide market and 80% of the seed coating agent market.

Aquaporins mainly promote two-way transmembrane movement of water. Aquaporin-mediated free water is rapidly and passively transported across a biomembrane, and is the main way for water to enter and exit cells. Generally, plant aquaporins are all members of the MIP superfamily. Aquaporins in different plants have highly homologous molecular structures and very conserved sequences. In terms of molecular structure, there are typical 6 transmembrane domains and 5 rings, which are named A, B, C, D and E rings, respectively. All members contain a very highly conserved NPA structure (Asn-Pro-Ala, NPA) in the B ring and the E ring. Johanson et al. (Johanson U. The complete set of genes encoding major intrinsic proteins in *Arabidopsis* provides a framework for a new nomenclature for major intrinsic proteins in plants. Plant Physiology, 2001, 126(4): 1358-69.) divide aquaporins, according to amino acid sequence homology and subcellular localization, into 5 families: plasma membrane intrinsic proteins (PIPs), tonoplast intrinsic proteins (TIPs), Nodulin 26-like intrinsic proteins (NIPs), small basic intrinsic proteins (SIPs) and GlpF-like intrinsic proteins (GIPs). In addition to the 5 types of aquaporins above, *Sphaerotheciella* also contains 2 new types of XIPs and HIPs. (Bienert G P, Bienert M D, Jahn T P, et al. Solanaceae XIPs are plasma membrane aquaporins that facilitate the transport of many uncharged substrates. Plant Journal, 2011, 66(2):306-317.).

In addition to transporting water molecules, studies have found that aquaporins can also transport some small molecules such as glycerol, silicic acid, ammonium, urea, boric acid, CO2, arsenite, H2O2, and ammonia. Some Solanaceae XIPs can also promote the transport of some neutral molecules such as glycerol and urea. In *Arabidopsis thaliana*, AtNIP6;1 and AtNIP7;1 are involved in the transport of boron and can adjust the nutrient distribution ratio of boron in the aboveground part and pollen (Li T, Choi W G, Wallace I S, et al. *Arabidopsis thaliana* NIP7;1: an anther-specific boric acid transporter of the aquaporin superfamily regulated by an unusual tyrosine in helix 2 of the transport pore. Biochemistry, 2011, 50(31): 6633-6641.). Terashima et al. (Terashima I, Ono K. Effects of HgCl2 on CO2 dependence of leaf photosynthesis: evidence indicating involvement of aquaporins in CO2 diffusion across the plasma membrane. Plant Cell Physiology, 2002, 43(1): 70-78.) proved that aquaporins can promote the transport of CO2 on the plasma membrane and improve photosynthesis of plants by using HgCl2 inhibitors. A functional expression experiment of yeast cells and *Xenopus* oocytes showed that ZmPIP1;5 and ZmPIP1;6 can improve the transport of CO2 in *Arabidopsis thaliana* guard cells (Heinen R B, Bienert G P, Cohen D, et al. Expression and characterization of plasma membrane aquaporins in stomatal complexes of *Zea mays*. Plant Molecular Biology, 2014, 86(3):335-350.). Rice OsNIP2;1, OsNIP1;1 and OsNIP3;3 are involved in arsenite uptake in rice, and OsNIP3;2 is involved in trivalent arsenic uptake in rice (Chen Y, Sun S K, Tang Z, et al. The Nodulin 26-like intrinsic membrane protein OsNIP3;2 is involved in arsenite uptake by lateral roots in rice. Journal of Experimental Botany, 2017, 68(11):3007-3016.; Sun S K, Chen Y, Che J, et al. Decreasing arsenic accumulation in rice by overexpressing OsNIP1;1 and OsNIP3;1 through disrupting arsenite radial transport in roots. New Phytologist, 2018.). Studies of Moller et al. (Moller I M. Plant mitochondria and oxidative stress: electron transport, NADPH turnover, and metabolism of reactive oxygen species. Annual Review of Plant Biology, 2001, 52(4):561-591.) showed that AQP8 can promote the release of $H_2O_2$ from the mitochondrial matrix.

However, the current reports related to aquaporins involve a number of small molecules with large differences in structure, but larger molecules (such as neonicotinoid insecticides) have not yet been reported related to promotion of transport function.

SUMMARY OF THE INVENTION

In view of the problems above, the disclosure is directed to provide a new plasma membrane intrinsic aquaporin responsible for transmembrane transport of neonicotinoid insecticides and an encoding gene thereof. The gene is a DNA molecule isolated from Chinese cabbage, named BraPIP2;1 by the applicant. The disclosure also provides application of the plasma membrane intrinsic aquaporin in improving the transport efficiency of plant neonicotinoid insecticide thiamethoxam.

Specifically, the disclosure is implemented through the following technical solutions:

First, an embodiment of the disclosure provides a plasma membrane intrinsic aquaporin, having an amino acid sequence as set forth in SEQ ID NO. 2. The plasma membrane intrinsic aquaporin is derived from Chinese cabbage and is located on the plasma membrane. Through a molecular docking technology, it is found that neonicotinoid insecticide molecules can pass through pores of the protein. Compared with an environment with no neonicotinoid insecticide (thiamethoxam, etc.) added, the plasma membrane intrinsic aquaporin has a significantly enhanced expression abundance in an environment with thiamethoxam added, and has the characteristics of powerfully mediating the transmembrane transport of thiamethoxam. Also, after an aquaporin inhibitor is added, the uptake of different neonicotinoid insecticides in Chinese cabbage can be inhibited.

Second, an embodiment of the disclosure provides an encoding gene BraPIP2;1 of a plasma membrane intrinsic aquaporin having an amino acid sequence as set forth in SEQ ID NO. 2, and the nucleotide encoding sequence of the encoding gene is as set forth in SEQ ID NO.1. A method for cloning the gene is as follows: the total RNA is extracted from the roots of Chinese cabbage by using an RNA simple Total RNA Kit (Tiangen Biotech, Beijing, China); according to the steps of a Primescript 1st Strand cDNA Synthesis Kit (Invirtrogen), 2 g of total RNA is used as a template and oligo (dT)18 is used as an anchor primer to synthesize 1st strand cDNA; according to the amino acid sequence information of PIP1;1 in the transcriptome analysis results of Chinese cabbage in our laboratory, a degenerate primer for a conserved region is designed; using the 1st strand cDNA synthesized above as a template, an ORF sequence is amplified by the degenerate full-length primer; and the amplified PCR product is sent for sequencing, and named BraPIP2;1 by the applicant.

Third, an embodiment of the disclosure provides a recombinant expression vector containing the encoding gene BraPIP2;1. Further, the recombinant expression vector is a *Saccharomyces cerevisiae* expression vector, and the *Saccharomyces cerevisiae* expression vector includes but is not limited to the vector pYES2.

Fourth, an embodiment of the disclosure provides a binary overexpression vector containing the encoding gene BraPIP2;1, and the binary overexpression vector includes but is not limited to the vector pCAMBIA2301.

Fifth, an embodiment of the disclosure provides application of the plasma membrane intrinsic aquaporin, having an amino acid sequence as set forth in SEQ ID NO. 2, in improving the uptake and transport efficiency of neonicotinoid insecticides in plants. The plants include at least one of *Arabidopsis thaliana*, vegetables (Chinese cabbage, etc.), rice, *Zea mays*, wheat and rape; and the neonicotinoid insecticides include one or more of thiamethoxam, imidacloprid, acetamiprid, nitenpyram, and dinotefuran.

Sixth, an embodiment of the disclosure discloses a method for promoting the uptake and transport of neonicotinoid insecticides in plants, including: introducing a binary overexpression vector containing a nucleotide sequence as set forth in SEQ ID No. 1 into plants for expression, thereby promoting the uptake and transport of the neonicotinoid insecticides in the plants. The binary overexpression vector includes but is not limited to the vector pCAMBIA2301; the plants are preferably at least one of vegetables, rice, *Zea mays*, wheat, rape, and *Arabidopsis thaliana*; and the neonicotinoid insecticides are preferably at least one of thiamethoxam, imidacloprid, acetamiprid, nitenpyram, and dinotefuran.

The disclosure found for the first time that aquaporins are involved in the transmembrane transport of neonicotinoid insecticides, also found for the first time the BraPIP2;1 gene resource in the plasma membrane intrinsic aquaporin and identified the functions thereof. The Chinese cabbage plasma membrane intrinsic aquaporin provided by the disclosure is mainly located in the plasma membrane, can mediate the transport of neonicotinoid molecules, and has the characteristic of sensitively responding to thiamethoxam in the external environment. At the same time, it has the function of rapidly mediating thiamethoxam across the cell membrane, promoting the accumulation of thiamethoxam in plants, which has important application value in the development of pesticides.

BRIEF DESCRIPTION OF THE DRAWINGS

FIG. 1 is a schematic diagram of subcellular localization of the BraPIP2;1 protein;

tobacco leaf cells instantaneously transformed for 48 hours under confocal microscope observation. Scale=40 μm.

FIG. 2 shows the effect of water channel inhibitors on the uptake of different neonicotinoid insecticides and nicotine in Chinese cabbage (FIG. 2A: thiamethoxam; FIG. 2B: imidacloprid; FIG. 2C: acetamiprid; FIG. 2D: nitenpyram; FIG. 2E: dinotefuran; and FIG. 2F: nicotine).

FIG. 3 shows the molecular docking analysis of BraPIP2;1 with different neonicotinoid insecticides and nicotine.

FIG. 4 is a schematic diagram of the expression characteristics of BraPIP2;1 and response characteristics thereof to thiamethoxam, where FIG. 4A shows the response characteristics of the root tissue BraPIP2;1 to external thiamethoxam; and FIG. 4B shows the response characteristics of the aboveground tissue BraPIP2;1 to external thiamethoxam.

FIG. 5 is a schematic diagram of the growth and the thiamethoxam content of a BraPIP2;1 recombinant yeast strain under thiamethoxam stress, where FIG. 5A shows the growth of the recombinant yeast under different concentrations of thiamethoxam; and FIG. 5B is a schematic diagram of the thiamethoxam content in the recombinant yeast strain.

FIG. 6 is a schematic diagram of the growth and the thiamethoxam content of BraPIP2;1 transgenic *Arabidopsis thaliana* plants under thiamethoxam stress, where FIG. 6A shows the growth of the transgenic *Arabidopsis thaliana* plants under different concentrations of thiamethoxam; FIG. 6B is a schematic diagram of the main root length of the transgenic *Arabidopsis thaliana* plants under different concentrations of thiamethoxam; FIG. 6C is a schematic diagram of the thiamethoxam content of the transgenic *Arabidopsis thaliana* plants; and BraPIP2;1#3 and BraPIP2;1#5 are overexpression *Arabidopsis thaliana* lines.

DETAILED DESCRIPTION OF THE INVENTION

The technical solutions of the disclosure will be further described below in conjunction with examples.

Example 1 Cloning and Analysis of the Full-Length Encoding Region of the BraPIP2;1 Gene 1. ORF Amplification of BraPIP2;1

The total RNA was extracted from a root sample of Chinese cabbage according to operation steps of using an RNA simple Total RNA Kit (Tiangen Biotech, Beijing, China). Using 2 g of total RNA as a template and oligo (dT)18 as an anchor primer, and referring to instructions of a Primescript 1st Strand cDNA Synthesis Kit (Invirtrogen), 1st strand cDNA was synthesized. Primers were designed to perform PCR amplification to obtain a single cDNA fragment, and the primer sequences are as follows: upstream primer sequence (SEQ ID NO.3): ATGGCGAAGGACGTGGAAGC; and downstream primer sequence (SEQ ID NO.4): TTAAACGTTGGCAGCACTTCTG.

An amplification system is 50.0 µL in total volume, including 20 ng of cDNA, 10.0 µL of 5×Prime STAR buffer, 4.0 µL of 2.5 mmol·L-1 dNTPs, 2.0 µL of 10 mmol·L-1 forward primer and reverse primer each, 1.25 U of PrimeSTAR HS DNA Polymerase, and the balance of redistilled water.

An amplification program is: pre-denaturation at 95° C. for 5 min, denaturation at 98° C. for 10 s, renaturation at 55° C. for 15 s, and extension at 72V for 60 s, 35 cycles in total.

The PCR product was sent to Tsingke Biotechnology Co., Ltd. for sequencing. The sequencing result shows that the full-length cDNA sequence of BraPIP2;1 is 2550 bp. The cDNA of BraPIP2;1 and the amino acid sequence of a protein encoded by BraPIP2;1 are as set forth in SEQ ID No. 1 and SEQ ID No. 2, respectively.

Example 2 Subcellular Localization of BraPIP2;1

Referring to Liu et al. (Liu T, et al. Unconventionally secreted effectors of two filamentous pathogens target plant salicylate biosynthesis. Nat Commun 5, 4686. 2014), BraPIP2;1 was constructed into a subcellular localization vector pBinGFP4, and transformed into an *Agrobacterium* strain GV3101 (deposited in the laboratory of Jiangsu Academy of Agricultural Sciences) by a freeze-thaw method. Tobacco was transformed instantaneously, and fluorescence was observed under a fluorescence microscope after 48 h-60 h. It was found that the green fluorescent signal was mainly distributed on the cell membrane or nuclear membrane (see FIG. 1), indicating that BraPIP2;1 is mainly located on the cell membrane and nuclear membrane related to transmembrane transport.

Example 3 Inhibiting the Activity of Aquaporins can Reduce the Uptake and Accumulation of Neonicotinoid Pesticides in Vegetables Referring to the paper (Wenfeng W, Wan Q, Li Y, et al. Uptake, translocation and subcellular distribution of pesticides in Chinese cabbage (*Brassica rapa* var. *chinensis*)[J]. Ecotoxicology and Environmental Safety, 2019.), water channel inhibitors, mercuric chloride and glycerol, of different concentrations were added to equal volumes of Hoagland nutrient solutions containing 2 mg/L nicotine compounds (thiamethoxam, imidacloprid, acetamiprid, nitenpyram, dinotefuran and nicotine). After 48 h, the concentrations of the nicotine compounds in the Chinese cabbage plants (with three leaves and one bud) were determined respectively. Each treatment was repeated five times.

To determine whether aquaporins can transport the neonicotinoid insecticide molecules and nicotine, the water channel inhibitors mercuric chloride (HgCl2) and glycerol of different concentrations were added to equal volumes of nutrient solutions containing 2 mg/L of different neonicotinoid insecticides (thiamethoxam, imidacloprid, acetamiprid, nitenpyram and dinotefuran) and nicotine, and the concentrations of the nicotine compounds in the plants were determined respectively.

Figure 2:
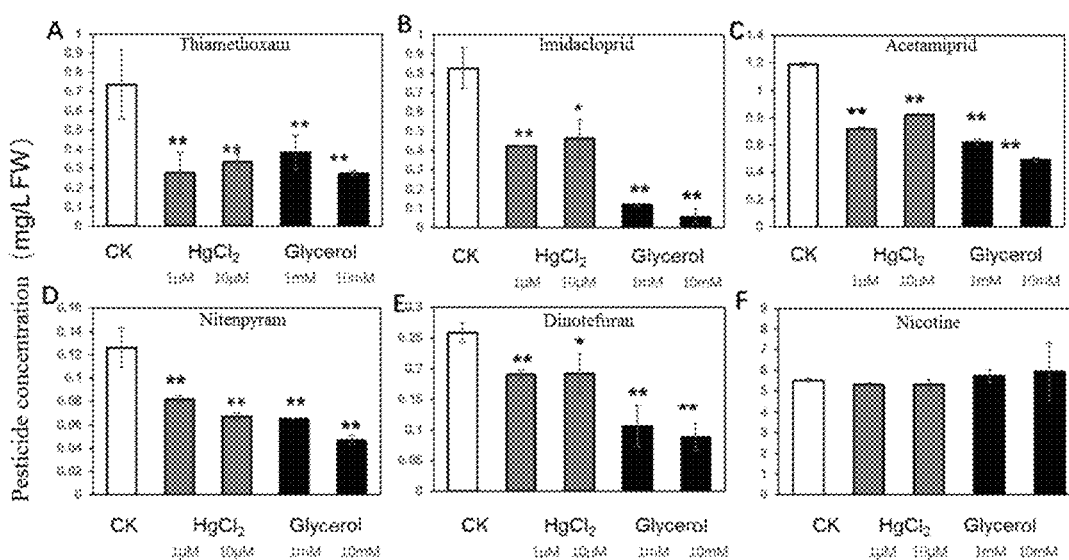

The test results are as shown in FIG. 2. After the water channel inhibitors were added, the content of the neonicotinoids in the plants was significantly reduced, while the content of nicotine in the plants did not change significantly. It can be seen that, the water channel inhibitors can significantly inhibit the uptake of the neonicotinoid insecticides in Chinese cabbage, but not the uptake of nicotine, indicating that the aquaporins are involved in the transmembrane transport of the neonicotinoid insecticides.

Example 4 Molecular Docking Analysis of BraPIP2;1 Protein with Different Neonicotinoids and Nicotine A 3D structure of BraPIP2;1 was obtained by homology modeling of the BraPIP2;1 amino acid sequence, and whether the neonicotinoid insecticide molecules (thiamethoxam, imidacloprid, acetamiprid, nitenpyram and dinotefuran) and nicotine molecules can pass through the pores in the middle of the BaPIP2;1 crystal structure was verified with the molecular docking technology. The docking range includes the whole protein conformation, so the docking results of the neonicotinoid insecticide molecules and nicotine molecules entering the central pores of the protein can be screened from many conformations generated to analyze whether the insecticide-like molecules can pass through the protein pores.

Figure 3:
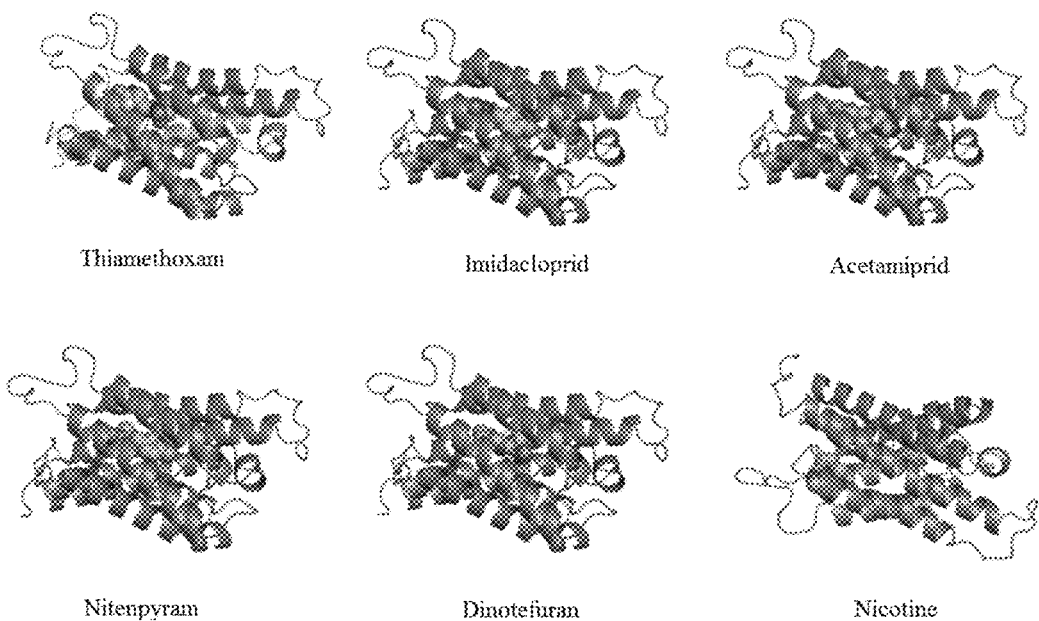

The software used for docking is AutoDockTools-1.5.6, the size of a docking box is set to 100 Å*126 Å*100 Å, semi-flexible docking is adopted, the algorithm uses the Lamarckian genetic algorithm, and the docking generates 200 results. The docking result is shown in FIG. 3: The neonicotinoid insecticide molecules (thiamethoxam, imidacloprid, acetamiprid, nitenpyram and dinotefuran) bind to the center of the protein channel, which proves that thiamethoxam and other neonicotinoid insecticide molecules do not produce steric hindrance when entering the channel. While the nicotine molecule cannot bind to the center of the protein channel, which proves that the nicotine molecule will produce steric hindrance when entering the channel.

The result above indicates that the BraPIP2;1 protein can transport neonicotinoid insecticides, but not nicotine.

Example 5 Response of the BraPIP2;1 Gene to Environmental Thiamethoxam Stress

Seedlings of Chinese cabbage with the same growth condition were put in a Hoagland's nutrient solution containing 10 mg/L thiamethoxam (the Hoagland's nutrient solution was purchased from Beijing Coolaber Technology Co., Ltd.), and treated in the Hoagland's nutrient solution for 6 and 24 hours (treatment group).

At the same time, a Hoagland's nutrient solution without thiamethoxam was used as the control group.

Treated root and aboveground tissue RNA of two groups was extracted respectively, the 1st strand cDNA was obtained by reverse transcription as a template, specific expression primers were designed based on the cDNA sequence of BraPIP2;1, the Chinese cabbage Tublin was used as an internal reference, and the expression of the gene transcription level was detected by quantitative RT-PCR.

Quantitative PCR primer design:
BraPIP2;1-F(SEQ ID NO 0.5): TCACTGGAACTGGAATCAACCC;
BraPIP2;1-R(SEQ ID NO 0.6): CCTGAAGCCCTCAAAACGAAC:

Tublin-F(SEQ ID NO. 7): ACTGGGTGTTTTGGGTTGGG;

Tublin-R(SEQ ID NO. 8): TGAAGGGGATTGCTCTGATGAC.

The quantification instrument is 7500 Real Time PCR System (Applied Biosystem), and a qPCRT system was configured according to the instructions of a kit 2×TSINGKE Master qPCR Mix (Tsingke Biotechnology Co., Ltd.). The PCR program is: pre-denaturation at 95° C. for 10 min, at 95° C. for 15s, and at 60° C. for 20 s, for 40 cycles.

Figure 4:
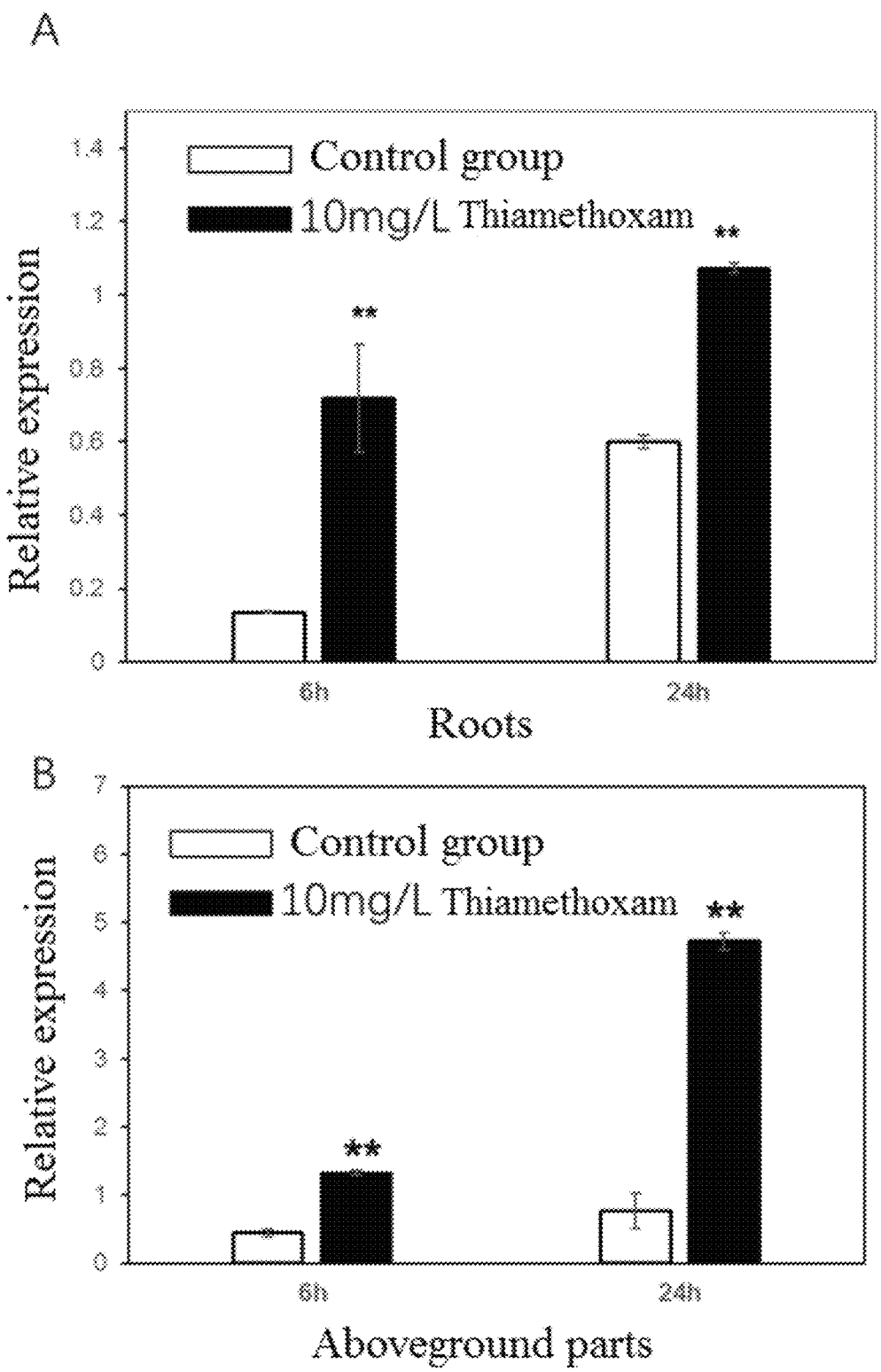

The result of qRT-PCR showed that BraPIP2;1 was expressed both in roots and aboveground parts. Compared with the control, under the condition of adding thiamethoxam, the expression abundance of BraPIP2;1 in the roots and aboveground parts was significantly increased after 6 hours and 24 hours of treatment (p<0.001) (as shown in FIG. 4), indicating that the transport and utilization of thiamethoxam is related to the BraPIP2;1 aquaporin.

Example 6 Overexpression of BraPIP2;1 Gene *Saccharomyces cerevisiae* can Improve Stress Tolerance to Thiamethoxam The BraPIP2;1 gene cloned in Example 1 was constructed into the *Saccharomyces cerevisiae* overexpression vector pYES2 (purchased from Clotech) referring to (He Lin, Jiang Lili, Wang Yucheng, Analysis of the stress tolerance of *Tamarix* thioredoxin peroxidase (ThPrx1) gene transformed into yeast, Journal of Northeast Forestry University, 2011, Vol. 39. No. 4, 101-104), and the constructed recombinant plasmid was named pYES2-BraPIP2;1. The pYES2-BraPIP2;1 and an empty vector pYES2 were transformed into *Saccharomyces cerevisiae* INVSc1 by lithium acetate precipitation. The recombinant yeasts were named INVSc1 (pYES2-BraPIP2;1) and INVSc1 (pYES2), respectively.

Induction of recombinant strains: Single colonies of the control yeast INvsc1 (pYES2) and the recombinant yeast INvsc1 (pYES2-BraPIP2;1) were picked, inoculated in an SC-U liquid medium (with glucose of a final concentration of 2%) respectively, and incubated at 30° C. for 24 h on a shaker. The OD600 value is measured, and the amount of bacterial solution required is calculated such that the OD600 of bacteria in 10 ml of induction medium (SC-U+2% galactose) is 0.4. Induce expression was carried out at 30° C. for 24 h. The OD600 value was measured again, and the amount of bacterial solution required was calculated.

Growth experiment of the recombinant strains under thiamethoxam stress: Referring to the method disclosed in (He Lin, Jiang Lili, Wang Yucheng, Analysis of the stress tolerance of *Tamarix* thioredoxin peroxidase (ThPrx1) gene transformed into yeast, Journal of Northeast Forestry University, 2011, Vol. 39. No. 4, 101-104), the OD600 value of the induced bacterial solution is measured, and the amount of bacterial solution required is calculated such that the OD600 of bacteria in 200 μL of bacterial solution is 2. The bacterial solution was centrifuged at 8500 r/min for 1 min, and the supernatant was discarded.

Figure 5:
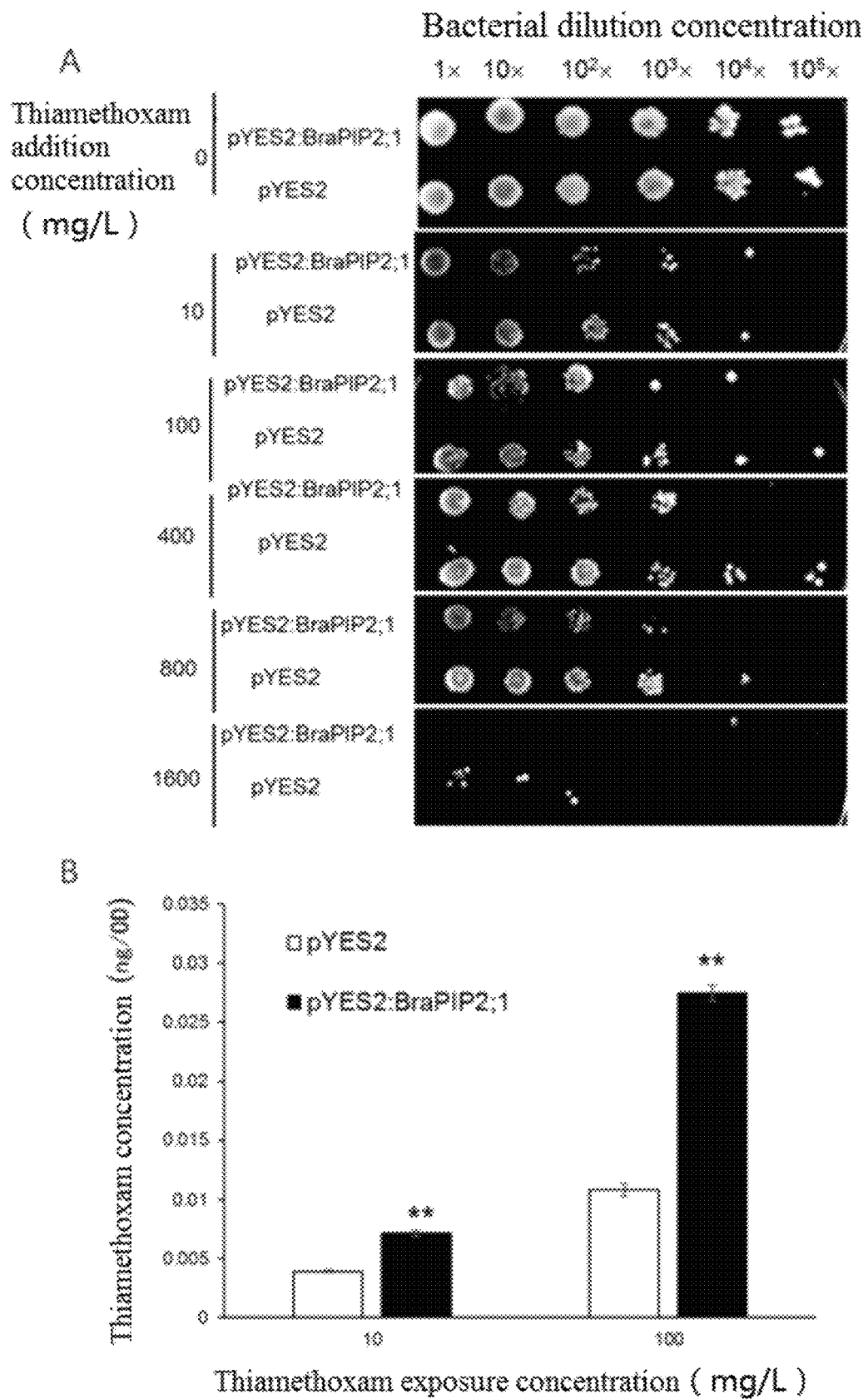

Thiamethoxam stress treatment: The bacteria were resuspended in 200 μL of thiamethoxam solutions of 0, 10, 100, 400, 800 and 1600 mg/L respectively, and subjected to stress at 30° C. for 72 h. The bacterial solutions were diluted by 10, 100, 1000, 10000 and 100000 times, and then 3 μL of bacterial solutions were spread on a solid medium of SC-U (with glucose of a final concentration of 2%), and incubated at 30° C. for 48 h. The result is as shown in FIG. 5A: The transgenic strain (pYES2-BraPIP2;1) grows the same as the wild strain (pYES2) without the thiamethoxam, and grows significantly weaker than the wild strain with the thiamethoxam.

The thiamethoxam content experiment of the recombinant strains: The OD600 value of the induced bacterial solution was measured and the amount of bacterial solution required was calculated such that the OD600 of bacteria in 500 ml of bacterial solution is 0.1. The bacterial solution was centrifuged at 8500 r/min for 1 min, and the supernatant was discarded. The bacteria were resuspended in 500 ml of SC-U liquid media containing 10 and 100 mg/L thiamethoxam (with glucose of a final concentration of 2%) respectively, and subjected to stress at 30° C. for 6 h, and the OD600 value was determined. After centrifugation at 6000 rpm for 10 min, the bacteria were washed three times with ultrapure water, and disrupted with glass beads combined with ultrasound, and thiamethoxam was extracted to measure the amount. Under the stress of 10 mg/L thiamethoxam, the thiamethoxam content of the recombinant strain was 0.0071 ng/OD, which was significantly higher than that of the control strain (0.0038 ng/OD). Under the stress of 100 mg/L thiamethoxam, the thiamethoxam content of the recombinant strain (pYES2-BraPIP2;1) was 0.028 ng/OD, which was significantly higher than that of the control strain (pYES2, 0.011 ng/OD) (see FIG. 5B).

Example 7 Overexpression of BraPIP2;1 Gene in *Arabidopsis thaliana* can Increase the Uptake and Accumulation of Thiamethoxam in *Arabidopsis thaliana*

The BraPIP2;1 gene cloned in Example 1 was constructed into the plant binary overexpression vector pCAMBIA2301 (purchased from Clotech). By the *Agrobacterium tumefaciens*-mediated method (Valvekens, D., van Montagu, M., and Lijsebettens, M. V. (1988). *Agrobacterium tumefaciens*-mediated transformation of *Arabidopsis thaliana* root explants by using kanamycin selection. Proc. Natl. Acad. Sci. USA 85, 5536-5540.), the inflorescence of wild-type *Arabidopsis thaliana* Col-0 (purchased from ATCC, USA) was infected with the constructed overexpression vector. Through screening (resistance pure line seedlings were screened on a 1/2MS plate containing 50 μg/mL kanamycin), BraPIP2;1 overexpression *Arabidopsis thaliana* pure line materials BraPIP2;1#3 and BraPIP2;1#5 were identified and obtained.

Figure 6:
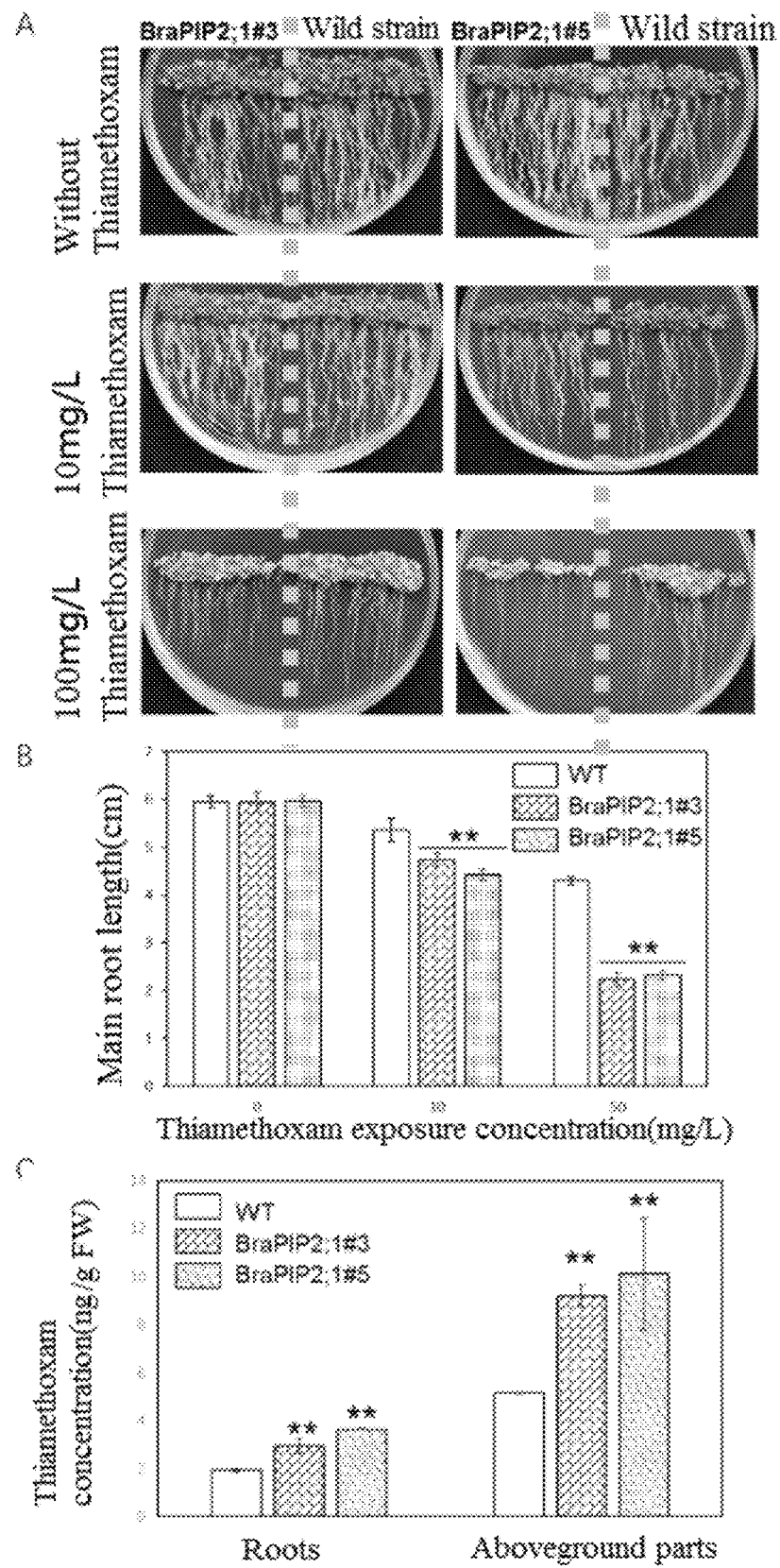

The pure line seeds of the BraPIP2;1#3 and BraPIP2;1#5 obtained in the previous transgenic experiment and a wild-type Col-0 material (WT) were germinated on a 1/2MS medium respectively, and then transferred to 1/2MS media (Qingdao Hopebio Co., Ltd., Item No. HB8469-12, PH=5.6) containing 10 and 50 mg/L thiamethoxam respectively. After 20 days, the growth of the seedlings was observed and the main root length was measured. The result is as shown in FIGS. 6A and 6B respectively. The main root length of the transgenic strain is shorter than that of the wild type.

In addition, germinated seedlings of the same size were transplanted into soil containing 10 mg/L thiamethoxam, and after 20 days of culture, the root and aboveground samples of the transgenic *Arabidopsis thaliana* and the control were harvested respectively, washed with deionized water, and weighed. The thiamethoxam content of each sample was measured and calculated with reference to (Wenfeng W, Wan Q, Li Y, et al. Uptake, translocation and subcellular distribution of pesticides in Chinese cabbage (*Brassica rapa* var. *chinensis*)[J]. Ecotoxicology and Environmental Safety, 2019.). The result is as shown in FIG. 6C.

The thiamethoxam content of the roots and aboveground parts of the transgenic plant is higher than that of the wild plant.

The examples above illustrate that the aquaporin BraPIP2;1 gene resource has the characteristic of sensitively responding to neonicotinoid insecticides in the external environment. At the same time, it has the function of rapidly mediating the uptake and transport of neonicotinoid pesticides, promoting the accumulation of neonicotinoid pesticides in plants, which has important application value in improving (agricultural) crop utilization of pesticides and pesticide development, and lays a foundation for further improvement of pesticide structure and development of systemic pesticides to improve pesticide utilization.

The invention claimed is:

1. A method for promoting uptake and transport of neonicotinoid insecticides in a plant, the method comprising introducing a binary overexpression vector containing a nucleotide sequence as set forth in SEQ ID NO: 1 into the plant for expression;

applying neonicotinoid insecticides to the plant or its environment; and measuring a concentration of neonicotinoid insecticides in root and above ground portion of the plant, wherein the plant has an increased concentration of the neonicotinoid insecticides as compared to that of a control plant that has not been transformed with the binary overexpression vector containing the nucleotide sequence as set forth in SEQ ID NO: 1.

2. The method for promoting uptake and transport of neonicotinoid insecticides in plants of claim 1, wherein the plants comprise at least one of vegetables, rice, *Zea mays*, wheat, rape and *Arabidopsis thaliana.*

3. The method for promoting uptake and transportation of neonicotinoid insecticides in plants of claim 1, wherein the neonicotinoid insecticides comprise at least one of thiamethoxam, imidacloprid, acetamiprid, nitenpyram and dinotefuran.

4. The method of claim 1, wherein the increase in concentration of neonicotinoid insecticide is at least 50% in roots and 80% in above ground portion of the plants.

* * * * *